United States Patent
van Beek et al.

(10) Patent No.: US 9,972,474 B2
(45) Date of Patent: May 15, 2018

(54) ELECTRON MICROSCOPE WITH MULTIPLE TYPES OF INTEGRATED X-RAY DETECTORS ARRANGED IN AN ARRAY

(71) Applicant: FEI Company, Hillsboro, OR (US)

(72) Inventors: Cornelis van Beek, Pittsburgh, PA (US); Frederick H. Schamber, Murrysville, PA (US); N. William Parker, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 0 days. days.

(21) Appl. No.: 15/224,628

(22) Filed: Jul. 31, 2016

(65) Prior Publication Data

US 2018/0033589 A1    Feb. 1, 2018

(51) Int. Cl.
*H01J 37/00* (2006.01)
*H01J 37/244* (2006.01)
(Continued)

(52) U.S. Cl.
CPC ........ *H01J 37/244* (2013.01); *G01N 23/2252* (2013.01); *H01J 37/16* (2013.01);
(Continued)

(58) Field of Classification Search
CPC ...... H01J 37/244; H01J 23/2252; H01J 37/16; H01J 37/18; H01J 37/20; H01J 37/26;
(Continued)

(56) References Cited

U.S. PATENT DOCUMENTS 4,317,036 A    2/1982    Wang
4,519,092 A    5/1985    Albert
(Continued)

FOREIGN PATENT DOCUMENTS

DE    19546142 A1    6/1997
EP    1650871 A1    4/2006
(Continued)

OTHER PUBLICATIONS

Leutenegger, P. et al., "Silicon Drift Detectors as Radiation Monitor for X-Gamma Rays and Particles". Proceedings of SPIE—The International Society for Optical Engineering, Jan. 1, 2000, pp. 579-591, vol. 4012.

(Continued)

*Primary Examiner* — Wyatt Stoffa
*Assistant Examiner* — Hanway Chang
(74) *Attorney, Agent, or Firm* — Scheinberg & Associates, P.C.; Michael O. Scheinberg

(57) ABSTRACT

An electron microscope including a vacuum chamber for containing a specimen to be analyzed, an optics column, including an electron source and a final probe forming lens, for focusing electrons emitted from the electron source, a specimen stage positioned in the vacuum chamber under the probe forming lens for holding the specimen, and multiple x-ray detectors positioned within the vacuum chamber, at different takeoff angles with respect to the sample's x-ray emission position in the chamber. Takeoff angles are provided to improve the counting efficiency of the various sensors. Multiple detectors of different types may be supported within the vacuum chamber on a mechanical support system, which may be adjustable. A method includes operating the sensors to optimize the time required for accurate x-ray counting by gathering data at the multiple takeoff angles.

19 Claims, 8 Drawing Sheets

(51) Int. Cl.
*H01J 37/16* (2006.01)
*H01J 37/18* (2006.01)
*H01J 37/20* (2006.01)
*G01N 23/225* (2018.01)
*H01J 37/26* (2006.01)

(52) U.S. Cl.
CPC .............. *H01J 37/18* (2013.01); *H01J 37/20* (2013.01); *H01J 37/26* (2013.01); *H01J 2237/164* (2013.01); *H01J 2237/2448* (2013.01); *H01J 2237/24475* (2013.01)

(58) Field of Classification Search
CPC ....... H01J 2237/164; H01J 2237/24475; H01J 2237/2448; G01N 23/2252
USPC .............................. 250/306, 307, 310, 311
See application file for complete search history.

(56) References Cited

U.S. PATENT DOCUMENTS

| | | | |
|---|---|---|---|
| 5,450,463 | A | 9/1995 | Iketaki |
| 5,481,109 | A | 1/1996 | Ninomiya et al. |
| 5,517,033 | A | 5/1996 | Krivanek et al. |
| 5,590,168 | A | 12/1996 | Iketaki |
| 5,594,246 | A | 1/1997 | Sudo et al. |
| 5,755,877 | A | 5/1998 | Kamakura et al. |
| 5,816,052 | A | 10/1998 | Foote et al. |
| 5,877,498 | A | 3/1999 | Sugimoto et al. |
| 6,396,061 | B1 | 5/2002 | Madden et al. |
| 6,421,415 | B1 | 7/2002 | Peczkis et al. |
| 6,448,555 | B1 | 9/2002 | Hosokawa |
| 6,452,177 | B1 | 9/2002 | Feldman et al. |
| 6,590,210 | B1 | 7/2003 | Essers |
| 6,797,953 | B2 | 9/2004 | Gerlach et al. |
| 7,109,486 | B1 | 9/2006 | Spallas et al. |
| 7,202,475 | B1 | 4/2007 | Testoni |
| 7,227,143 | B2 | 6/2007 | Choi |
| 7,261,465 | B2 | 8/2007 | Butzine et al. |
| 7,335,895 | B1 | 2/2008 | Spallas et al. |
| 7,339,175 | B1 | 3/2008 | Drummond et al. |
| 7,378,664 | B1 | 5/2008 | Howard et al. |
| 7,906,762 | B2 | 3/2011 | Bierhoff et al. |
| 7,910,888 | B2 | 3/2011 | Tanaka et al. |
| 8,080,791 | B2 | 12/2011 | Harrach et al. |
| 8,093,558 | B2 | 1/2012 | Buijsse |
| 8,154,185 | B2 | 4/2012 | Yang et al. |
| 8,164,059 | B2 | 4/2012 | Gerlach et al. |
| 8,309,921 | B2 | 11/2012 | Bierhoff et al. |
| 8,311,183 | B2 | 11/2012 | O'Dwyer et al. |
| 8,334,511 | B2 | 12/2012 | Schamber et al. |
| 8,987,665 | B2 | 3/2015 | Schamber et al. |
| 2006/0016990 | A1 | 1/2006 | Suzuki et al. |
| 2006/0138325 | A1 | 6/2006 | Choi |
| 2006/0226340 | A1 | 10/2006 | Sasayama et al. |
| 2007/0145266 | A1 | 6/2007 | Cohen et al. |
| 2007/0153980 | A1 | 7/2007 | Butzine et al. |
| 2008/0121801 | A1 | 5/2008 | Howard et al. |
| 2008/0156996 | A1 | 7/2008 | Nicolosi et al. |
| 2008/0191598 | A1 | 8/2008 | Yang et al. |
| 2010/0148064 | A1 | 6/2010 | Harrach et al. |
| 2010/0171037 | A1 | 7/2010 | Bierhoff et al. |
| 2010/0230590 | A1 | 9/2010 | Bierhoff et al. |
| 2010/0303206 | A1 | 12/2010 | O'Dwyer et al. |
| 2012/0074333 | A1 | 3/2012 | Harrach et al. |
| 2012/0199738 | A1 | 8/2012 | Gerlach et al. |
| 2013/0299698 | A1 | 11/2013 | Schamber et al. |
| 2015/0235726 | A1 | 8/2015 | Ohashi et al. |
| 2016/0020067 | A1 | 1/2016 | Iwasawa |
| 2016/0189922 | A1 | 6/2016 | Kooijman et al. |

FOREIGN PATENT DOCUMENTS

| | | |
|---|---|---|
| EP | 2197019 A2 | 6/2010 |
| GB | 1232878 A | 5/1971 |
| JP | 59061794 | 4/1984 |
| JP | H08222172 A | 8/1996 |
| WO | 1998014979 A1 | 4/1998 |

OTHER PUBLICATIONS

Von Harrach, HS, et al., "An Integrated Multiple Silicon Drift Detector System for Transmission Electron Microscopes" Journal of Physics, 2010, 4 pgs, vol. 241, No. 1.

Zaluzec, Nestor J., "Innovative Instrumentation for Analysis of Nanoparticles: The π Steradian Detector," Microscopy Today, Jul. 2009, pp. 56-59, Cambridge University Press, New York, NY, USA.

Isakozawa, S. et al., "The development of a new windowless XEDS detector," Journal of Microscopy 59 (6), (2010), pp. 469-472.

Lyman, C.E. et al., "X-Ray Detectors and Spectrometers," Ultramicroscopy 28 (1989) pp. 137-149, North-Holland Amsterdam.

ELECTRON MICROSCOPE WITH MULTIPLE TYPES OF INTEGRATED X-RAY DETECTORS ARRANGED IN AN ARRAY

CROSS REFERENCE TO RELATED APPLICATIONS

N/A.

BACKGROUND OF THE INVENTION

1. Field of the Invention

The invention pertains to the integration of semiconductor x-ray radiation sensors within a Scanning Electron Microscope (SEM) or similar analytical electron-beam instrument. The invention pertains to novel structures and methods of configuring both the detection elements and the microscope, and operating the x-ray detectors, so as to achieve improvements in performance and economies of construction, as well as other benefits.

2. Background

The installation of a solid-state Energy Dispersive X-ray (EDX) detector onto an electron microscope was first reported by Fitzgerald, Keil, and Heinrich in 1968. The type of detector described was a lithium-drifted silicon (Si(Li)) diode that was introduced through the port of an electron probe micro analyzer (EPMA). This kind of detector was soon commercialized and units of this same general type have been installed on many kinds of Electron Microscope (EM), notably including the Electron Probe Micro-Analyzer (EPMA), Scanning Electron Microscope (SEM), Transmission Electron Microscope (TEM), and Scanning Transmission Electron Microscope (STEM). Though the technology has been greatly refined over the years, the EDX units themselves have retained certain significant characteristics of the earliest models.

Pertaining to the interface of an EDX detector to an electron microscope of the SEM/EPMA type (which is the field of the subject invention), there are several important considerations affecting the performance of the detector:

(a) A large detection solid angle is desirable in order to maximize the number of detected x-rays (and thus the statistical precision) that can be achieved for a given beam current and measurement time.

(b) A high take-off angle is desirable in order to minimize absorption effects as the excited x-rays exit from a point of origin below the surface of the specimen.

(c) Optimal collimation of the detected x-rays is facilitated by pointing the detector coaxially at the intended beam impact point on the specimen. Such collimation ensures that only the uniformly responsive area of the sensor is employed for detection and that x-rays originating from scattered electrons are excluded.

Thus, in an "ideal" situation, the sensor element would be located very close to the specimen, with its axis in line with the intended beam impact point, and inclined at a high take-off angle. However, it is also desirable for the focusing lens of the microscope to be in close proximity to the specimen and, for the many applications in which a backscattered electron detector is required, that the BSE detector's view of the specimen should not be obscured. Thus, the space under the focusing lens is both small and crowded and this restricts the attainment of ideal detector geometry. Further, the physical arrangement of the specimen chamber, such as the presence of access doors and auxiliary ports, will play a large role in restricting where and how detectors may be placed.

It can be appreciated that the above considerations, when coupled with the over-riding necessity of thermally coupling the Si(Li) sensor to an external cryogenic cooler, have shaped the evolution of the traditional EDX detector unit into the familiar tube-mounted configuration (which has sometimes been descriptively referred to as a "sensor on a stick"). In turn, the standardization on this kind of tube-mounted configuration has also affected the design of electron microscopes which, by necessity, are specifically configured for mounting of such detectors. Since x-ray detectors have historically been designed and manufactured by one group of suppliers and electron microscopes by another, departure from this familiar model has not been attractive to either group.

Within the past decade, the technology of EDX detectors has been radically altered by the introduction of highly capable x-ray sensors that do not require cryogenic cooling. The principal current embodiment of this type of detector is the so-called "silicon drift detector" (SDD) whose operation is described in the scientific literature. These devices achieve spectroscopic performance generally superior to that of the Si(Li) detector, but at temperatures that can be conveniently achieved with a small thermoelectric cooler (TEC) based on the Peltier principle.

Collection efficiency is one of the most important characteristics of an EDX detector since it dictates the speed and precision of measurements. One strategy for improving collection efficiency is to increase the active area of the sensor, thereby increasing the solid angle. For the Si(Li) detector, this strategy is limited by the direct relationship between detector noise and active area, meaning that resolution rapidly degrades as detector size increases. Consequently, Si(Li) detectors with active areas of greater than 30 $mm^2$ have rarely been used in EM applications. The technology of the SDD detector, on the other hand, largely decouples the detector area from the noise characteristic, so that SDD performance is much less affected by the active area of this type of sensor. Consequently, 80 $mm^2$ SDD detector units are now marketed for electron microscope applications and suitable packaged sensor modules of area up to 100 $mm^2$ are commercially offered. Though such increases in detector size are certainly beneficial in certain respects, they also have drawbacks, and especially within the context of the conventional tubular-mount EDX design. The diameter of the detector tube must accommodate the size of the sensor device with allowance for mounting and connections, and this increased tube diameter limits the optimal placement of the detector. Because of the necessity of avoiding interferences with the final focusing lens, the BSE detector, and the specimen, a larger diameter detector must be somewhat retracted and/or operated at a lower takeoff angle. To avoid these consequences, it would be necessary to increase the working distance of the specimen to the face of the final focusing lens, which is in turn detrimental to the optical performance of the microscope. Thus, it will be appreciated that compromises and diminishing returns ensue when increased detector solid angle is accompanied by an increase in detector tube diameter.

In addition to such geometrical considerations, increasing the detection efficiency by increasing detector area creates other problems when there is a large flux of x-rays impinging on the detector. An SDD detector equipped with modem electronics can detect x-rays at rates upwards of 100,000 events/second. However, at such high rates there is also an increased probability of "summing events" in which two different x-ray emissions reach the detector so close together in time that they cannot be distinguished as separate events. This effect leads to "sum peaks" and other artifacts in the measured x-ray spectrum, and this in turn creates problems relative to accurate analysis. Thus, a large-area detector operated in close proximity to a specimen may be advantageous for analytical circumstances where the x-ray rate is low, but is problematic when the rate is high. Of course, the x-ray detection rate can always be reduced by either reducing the electron beam intensity, thereby reducing the number of x-rays produced, or by withdrawing the detector so as to reduce the solid angle (many detectors are mounted on slides for just this reason). However, exercising either of these strategies tends to defeat the point of a large-area detector, and neither of these strategies is optimal when the specimen has both high-emission and low-emission regions.

Finally, there are other, more subtle issues associated with very-large-area x-ray sensors. One is that the large sensitive area makes it more difficult to collimate the x-ray path to accept x-rays emitted from the point of beam impact and exclude those produced by scattered electrons striking elsewhere. Also, although the energy resolution of SDD detectors does not degrade as significantly as for the Si(Li) detector as the sensor area is increased, there is still some loss of resolution in the current generations of SDD devices. And finally, large-area SDD sensors of spectroscopic quality are substantially more expensive at present than smaller devices.

Thus, the strategy of increasing x-ray detection efficiency by increasing the area of the sensor element is a viable option up to a point, and then other factors increasingly diminish its attractiveness.

An alternative manner of increasing the x-ray detection efficiency has been to employ multiple detectors. This has sometimes been employed with Si(Li) detectors for specialized applications where x-ray collection speed is very important, the microscope is equipped with appropriate mounting ports, and the high cost is warranted. Since this strategy utilizes an independent set of counting electronics for each sensor element, this strategy for multiplying the effective detection solid angle can be accomplished without exacerbating the problem of summing events.

A strategy that can be employed to gain the benefits of multiple detectors without a proliferation of ports on the electron microscope is to incorporate multiple sensor elements in a single detector housing. This is an attractive option for SDD sensors because they are fabricated via semiconductor lithography technology. Thus it is possible to manufacture SDD arrays that incorporate multiple sensor elements in the same die, and such multi-element sensor arrays are commercially available for integration into an x-ray detector unit. A certain commercial detector unit mounts an array of four 10 mm$^2$ sensor elements in a single detector tube, with the array perpendicular to the axis of the tube, and provides each sensor with its own electronics processing channel. In this manner, the single detector provides an equivalent detection solid angle of a 40 mm$^2$ sensor, but can sustain much higher counting rates than a mono-element detector of this size due to the parallel processing electronics. However, because of the intrinsic size of such an array, this kind of detector requires an especially large mounting tube and thus again sacrifices some sensitivity due to setback from the specimen. Thus, this kind of detector is best suited for applications (such as EPMA analysis) where high beam currents are employed, and high count rate is more important than high-sensitivity.

Another commercial variant of the multi-element sensor array concept arranges the sensor elements around a central orifice. When implemented as a detector for electron microscopes, the sensor array is incorporated in a flat housing with a central passage for the beam. The housing is inserted under the final focusing lens of an electron microscope, immediately above the specimen so that the effect is that of four sensors arrayed around the axis of the beam. This arrangement can provide a favorable detection solid angle and thus provides high sensitivity, as well as the benefits of a symmetric detector array for analyzing rough specimens. However, this sensor occupies the position normally reserved for a BSE detector, and it is thus not suitable for the many applications where a high-quality BSE signal is required.

It is apparent that the multi-element SDD device can be a very effective means for achieving higher counting rates. Such detectors combine certain of the advantages of both the large area detector and multiple detectors.

U.S. Pat. No. 8,334,511, which is commonly owned by the owner of the present application, describes an electron microscope with integrated detectors. The detectors are arranged on a support structure at positions around the SEM column opening.

SUMMARY OF THE INVENTION

The present invention teaches a new approach to the design of an electron microscope, in which one or more energy-dispersive sensors are integrated directly into the structure of the microscope, thereby realizing a number of important benefits. The methods taught are directly applicable to SDD technology, but are also applicable to other types of solid-state x-ray sensor (such as the PIN diode, or CCD devices) which do not require liquid nitrogen cooling. Herein it is shown how the x-ray detector function may be advantageously positioned and integrated into the structure of the EM itself.

The type of electron microscope towards which the subject innovations are specifically directed is one of the SEM/EPMA type wherein the specimen stage is located exterior to and below the final focusing lens. However, certain beneficial aspects of the innovations herein taught may also be applicable to electron microscopes of other configurations.

The present invention in different aspects presents two primary features, one being the physical configuration of different types of x-ray detectors positioned at different takeoff angles within the electron microscope chamber, and the second pertaining to the methods of controlling the integrated x-ray detectors to improve the x-ray counting process of the microscope. Other aspects of the invention include computer readable media containing programming instructions for accomplishing the processes herein. Still further aspects involve the combination of an electron microscope and detectors configured and positioned according to the techniques herein.

The various aspects provide the benefits of much greater efficiency and accuracy in counting x-rays over time and identifying elemental composition therefrom, especially in cases where low energy elements must be identified in the sample. They also provide improved integration of x-ray detectors of multiple types (for different energy levels) positioned in a SEM vacuum chamber with backscattered electron detectors or other detectors. The counting or detection efficiency is improved, and the accuracy in distinguishing low-energy x-rays from noise is improved. The ability to integrate x-ray detectors into the SEM column is also improved, allowing for smaller structures and better shielding of x-ray and BSE detectors. Another aspect of the present invention is that it teaches a particularly efficient and economical manner of accommodating multiple sensors, resulting in novel configurations of sensors that have not heretofore been practiced as a single detector system.

With reference to the first feature, the electron microscope of the present invention is comprised of a vacuum chamber for containing a specimen to be analyzed, an optics column, including an electron source and a final probe forming lens, for focusing electrons emitted from the electron source, and a specimen stage positioned in the vacuum chamber under the probe forming lens for holding the specimen. The electron microscope further includes a first x-ray detector positioned within said vacuum chamber, said first x-ray detector including a first low energy x-ray sensitive solid-state sensor and a first mechanical support system supporting and positioning said first detector within said vacuum chamber positioned to sense x-rays at a high takeoff angle of between about 45 degrees and 90 degrees relative the specimen surface. A second x-ray detector is positioned within said vacuum chamber, and includes a second high energy x-ray sensitive solid-state sensor and a second mechanical support system supporting and positioning said second detector within said vacuum chamber positioned to sense x-rays at a low takeoff angle of between about 27 and 56 degrees relative the specimen surface, and lower than the first detector takeoff angle.

Some versions may include a third x-ray detector positioned within said vacuum chamber, said third x-ray detector including a third x-ray sensitive solid-state sensor having a thick beryllium window with a thickness of between 450-1000 micrometers and sensitive to very high energy x-rays and a third mechanical support system for supporting and positioning said third detector, including said third sensor, within said vacuum chamber positioned to sense x-rays at a lower takeoff angle than the second detector. In other versions the third detector may have no beryllium window but may be protected by other techniques.

In some variations, the first low energy sensor includes an ultra-thin window sensor fitted with x-ray optic that passes only x-rays in the range of energies released from the elements Li, B, C, N, O, and F. In other variations, the first low energy sensor may be a windowless sensor that is controlled to enter a first low energy sensing mode by opening a cover exposing the sensor to the x-rays, and controlled to enter a second mode by closing a cover blocking x-rays from the sensor. The first low energy sensor may include a collimator mounted above a sensor surface and configured for blocking x-rays at designated blocked energy levels, and passing x-rays at designated passing energy levels through to the sensor surface for detection.

In some variations the first low energy sensor may be integrated with the column of the microscope such that the first sensor is positioned inside of an arrangement of focusing electrodes of the optical column and further positioned above the lower ends of lens elements of the optics column to achieve a higher takeoff angle position that is shielded from backscattered electrons by bias voltages provided on the electrodes and lens elements. The second high energy sensor may be positioned outside of the optical column in this version. BSE detectors may be positioned at the lower side of the chamber with shields between BSE detectors and the sample. A large negative voltage may be provided on focusing electrodes to deflect the BSEs on a curved path around the shields, allowing them to be sensed on the BSE detectors, while the BSE detectors are shielded from x-rays.

A very-high-energy X-ray detector in this version may be positioned at a low takeoff angle. This detector may be integrated with a BSE repeller electrode, which includes at least some of the supporting structure of the detector and is biased at a large negative voltage, for example, about −16.1 kV, or a large negative voltage such as −16 kV or greater, or −20 kV or greater. A similar bias voltage may also be applied to the detector itself. The voltage required will vary with the energy of the beam and the bias voltage of the sample, which in this case is held a 0V. The voltage should be set at a sufficiently large value to repel the backscattered electrons from the surface of the very-high-energy detectors, and further curve the BSE's toward BSE detectors.

In some embodiments, the second high energy sensor is constructed with a silicon drift detector (SDD) sensor electrode having a large thickness of approximately 450-1000 micrometers.

In some embodiments, least one of the mechanical support systems supporting and positioning the first and second detectors is adjustable to change the position and takeoff angle of the relevant sensor. This mechanical support may be adjusted manually or by electrical control, in response to a configuration stored in a scan sequence. In some versions, both of the mechanical support systems supporting and positioning the first and second detectors are adjustable to change the position and takeoff angle of the relevant sensor.

Some embodiments include an additional sensor, of a type other than a solid-state x-ray sensor, the additional sensor also attached within said vacuum chamber to said support system. The additional sensor may be a backscattered electron detector.

According to a second aspect of the invention, a method is provided for examining a specimen using an electron microscope having a vacuum chamber for holding the specimen. The method includes (a) positioning the sample on a specimen stage within the vacuum chamber; (b) mechanically unshielding and activating a first set of one or more low energy x-ray sensors; (c) activating a second set of one or more high energy x-ray sensors, positioned to receive x-rays at a lower takeoff angle than that of a position of the first set of sensors; (d) activating a charged particle beam and then focusing and steering it toward desired target areas on the specimen to stimulate x-ray emission from the specimen; (e) while performing (d) detecting a first group of x-rays of varying energies incident on the first and second sensor sets, some of the x-rays detectable only on the first sensor set and some detectable on the second sensor set, and in response saving first scan data indicating a combined count of x-rays detected at multiple energy levels.

Other versions do not require the mechanically movable shielding on a low energy x-ray detector, but instead employ ultra-thin window detectors for the low-energy x-ray measurements, but follow a similar process of scanning and may incorporate the variations below similarly to the processes with a movable shielding.

Some variations of the method may include comparing the first scan data to a material library to determine a desired scan sequence for detailed x-ray scanning, and based on the scan sequence, activating selected sensors from the first and second sensor sets, then activating the charged particle beam again and detecting a second group of x-rays incident on the selected sensors, some of the x-rays detectable on less than all of the selected sensors.

The first set of low energy sensors may be operated with a relatively long integration time of 1 to 8 micro-seconds, while the first set of high energy sensors may be operated with a relatively short integration time constant of less than one micro-second. In other embodiments, the integration time may range from 1 to 32 micro-seconds. In still other embodiments, the integration time may be selected based on the energies and fluxes of the X-rays reaching the detectors.

In some versions, the method further includes scaling or adjusting the data relative to the takeoff angle of the sensor to account for the increased presence of x-rays at high takeoff angle positions.

According to another aspect, the invention covers a combination of elements including an electron microscope and multiple x-ray detectors, said microscope including a vacuum chamber containing a specimen stage for holding a specimen to be analyzed. The x-ray detectors include a first set of one or more low energy solid-state sensors, positioned within said vacuum chamber to sense x-rays at a high takeoff angle of between 45 degrees and 90 degrees relative the specimen surface, and a second set of one or more high energy solid-state sensors, positioned within said vacuum chamber to sense x-rays at a low takeoff angle of between 27 and 56 degrees relative the specimen surface, and lower than the take off of the first set of sensors.

The combination may also include a third set of one or more solid-state sensors sensitive to high energy x-rays, positioned within said vacuum chamber at a low takeoff angle of between 27 and 56 relative to the specimen surface. This third set may include a different type of sensor such as a dual layer sensor. The third set of sensors may be positioned at a lower takeoff angle than the second set of sensors.

The combination may include an adjustable mechanical support for said x-ray detectors, the adjustable mechanical support system allowing adjustment to the takeoff angle position of the sensors relative to the specimen surface. The adjustable mechanical support for said x-ray detectors may be operable under control of a system controller to adjust the takeoff angle position of at least one sensor relative to the specimen surface while the vacuum chamber is closed.

In some versions, at least one of said first set of low energy solid-state sensors includes a shield mechanically adjustable under control of a system processor to move to a first position shielding the sensor and second position allowing x-rays to reach the sensor.

The first set of one or more low energy solid-state sensors may include an ultra-thin window sensor fitted with x-ray optic that passes only x-rays at energies released from one or more of the elements Li, B, C, N, O, and F.

In some embodiments, the combination further includes a backscattered electron (BSE) detector positioned within the vacuum chamber near an electron beam entry location, where the BSE detector includes two sections in two quadrants of the area surrounding the beam entry location, and leaving gaps in the other two quadrants, and wherein the first set of low energy x-ray sensors are positioned close to the electron beam entry location at least partly in the gaps provided by the BSE in the other two quadrants.

In some embodiments, the first set of low energy solid-state sensors comprises one or more collimators mounted above a sensor surface of a respective one or more of the low energy solid state sensors and configured for blocking x-rays at designated blocked energy levels, and passing x-rays at designated passing energy levels through to the sensor surface for detection.

In some embodiments, the second set of high energy solid-state sensors comprises at least one sensor constructed with multiple layers of silicon-drift detector (SDD) sensor electrode, each layer activatable to detect x-rays that reach it.

Other objects and advantages appear hereinafter in the following description and claims. The accompanying drawings show, for the purpose of exemplification, without limiting the scope of the present invention or the appended claims, certain practical embodiments of the present invention.

Figure 4:
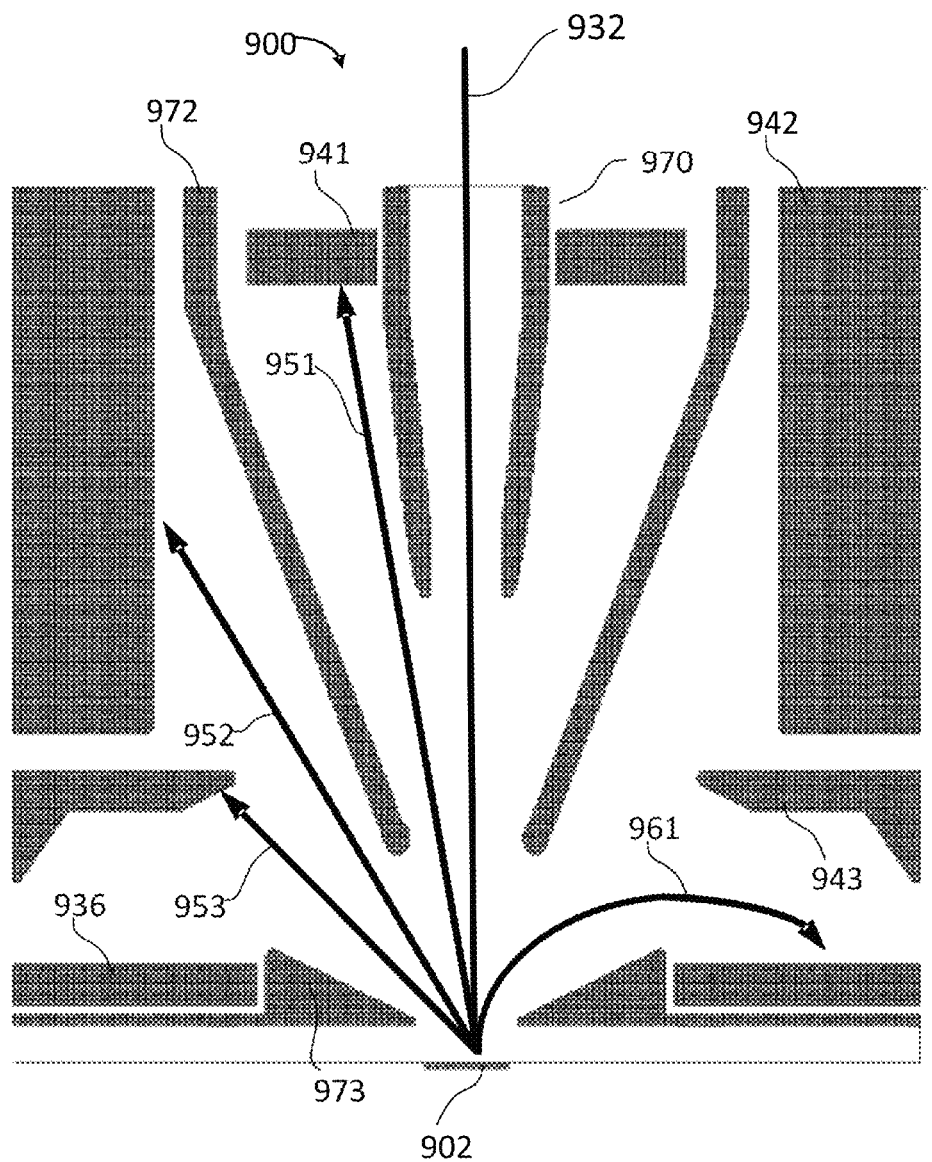
FIG. 4 is a cross-sectional diagram of a sensor arrangement according to another embodiment showing X-ray and BSE trajectory vectors.

The accompanying drawings are not intended to be drawn to scale, except generally the cross-section of FIG. 4. In the drawings, each identical or nearly identical component that is illustrated in various figures is represented by a like numeral. For purposes of clarity, not every component may be labeled in every drawing.

DETAILED DESCRIPTION OF EXAMPLE EMBODIMENTS

Several variations of the subject invention are now described in order to illustrate the salient features of the invention. The examples are chosen to illustrate how the key innovation—incorporation of the x-ray sensor into the structure of the microscope—facilitates a number of useful variations that can be achieved in conjunction with additional innovative elements. Not all of the innovative elements are employed in each of the illustrated examples.

Figure 1:
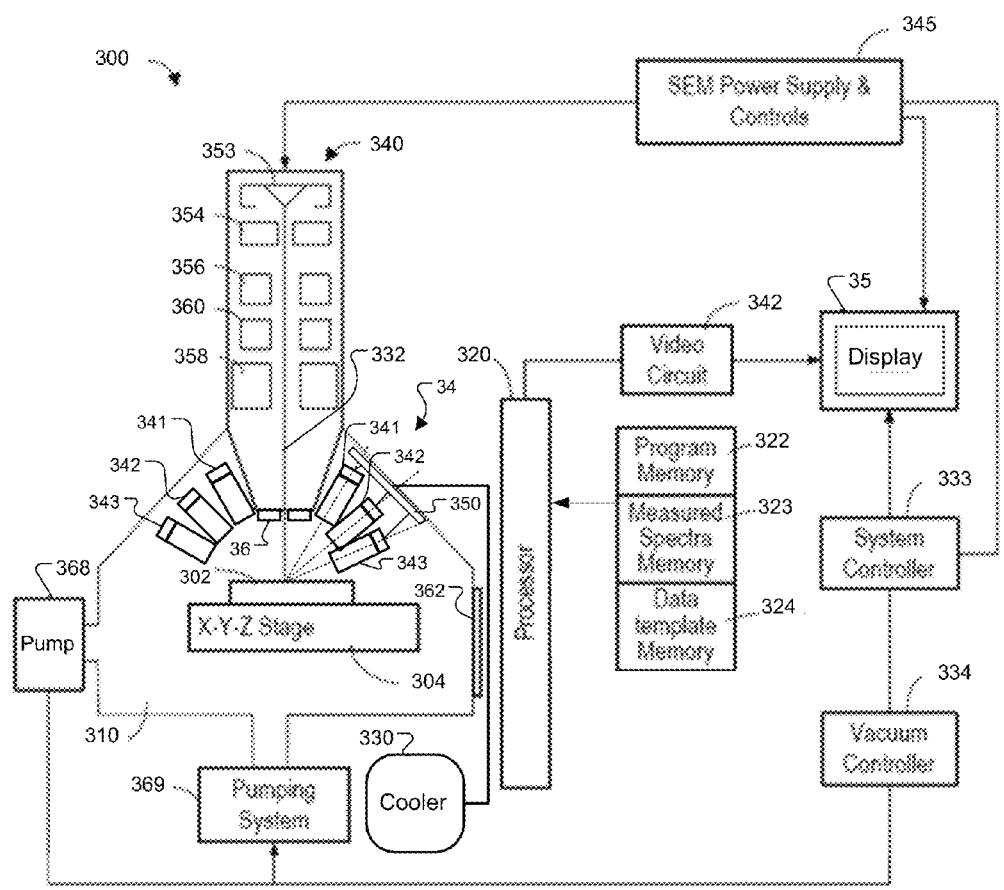
FIG. 1 is a block diagram of a scanning electron beam system 300 with x-ray detectors 341-343 suitable for analyzing samples according to an example embodiment of the present invention.

FIG. 1 shows an example of a scanning electron beam system 300 with x-ray detectors 341-343 suitable for analyzing samples according to an example embodiment of the present invention. A scanning electron microscope 340, along with power supply and control unit 345, is provided with system 300. An electron beam 332 is emitted from a cathode or other electron source 353 by applying voltage between cathode 353 and an anode 354. Electron beam 332 is focused to a fine spot by means of a condensing lens 356 and an objective lens 358. Electron beam 332 is scanned two-dimensionally on the specimen by means of a deflection coil 360. Operation of condensing lens 356, objective lens 358, and deflection coil 360 is controlled by power supply and control unit 345.

A system controller 333 controls the operations of the various parts of scanning electron beam system 300. The vacuum chamber 310 is evacuated with optional ion pump 368 and mechanical pumping system 369 under the control of vacuum controller 334.

Electron beam 332 can be focused onto sample 302, which is on movable X-Y stage 304 within lower vacuum chamber 310. When the electrons in the electron beam strike sample 302, the sample gives off x-rays whose energy is correlated to the elements in the sample. X-rays having energy inherent to the elemental composition of the sample are produced in the vicinity of the electron beam incident region. Emitted x-rays are collected by an array 34 of x-ray detectors 341, 342, and 343, which in this version employ SDD (silicon drift detector) x-ray sensors that are optimized for differing parts of the x-ray energy range. The detectors are preferably held by a mechanical support system 350, which may be a common, connected structure supporting the entire array 34, or may be separate systems for each of the sensors or each group of sensors at a common takeoff angle as discussed below. In some versions, at least one of the mechanical support system(s) 350 supporting and positioning the first and second detectors is adjustable to change the position and takeoff angle of the relevant sensor. In some versions all of the mechanical support system(s) 350 allow adjustment of the takeoff angle, which may be adjusted in a designated range for each system manually or by electrical control by processor 320, in response to a configuration stored in a scan sequence, as further described below.

While three types of detectors are labelled for illustration purposes, various embodiments may include other types of detectors including SDD and other x-ray detectors, including detectors selected from the list below of four distinct types of detectors, two of presently conventional types, and two of customized types:

1. Conventional UTW (ultra-thin window)—this is a high-quality SDD equipped with a ultra-thin window (UTW) and an electron trap. Its primary role is to produce well-resolved spectra of the lightest elements (typically boron through fluorine) though it will in fact provide coverage of the complete x-ray spectrum up to about 15 KV, but may have a floor of around 200 eV at the low end. Because it must be operated at relatively low count rate, it may be implemented as a small-area device, which aids the energy resolution and keeps the implementation cost low (for example, cheaper sensor, less stringent cooling, and a simpler electron trap).

2. Conventional BeW (beryllium window)—this is an SDD equipped with a beryllium window that limits detection to the elements sodium and above. Because energy resolution is not so critical for higher-energy x-rays, this can be a relatively large area device of less-than premium quality. Because it requires no electron trap, it can be located very close to the specimen.

3. Detector with low-energy optic. This is a UTW SDD detector equipped with an optical element mounted in front of the sensor that cuts off higher energy x-rays.

4. High-energy SDD. This is a specially designed SDD to optimize the efficiency for x-rays of 10 KeV and above (where normal SDD's begin to lose efficiency) and equipped with a moderately-thick Be window to filter out lower energies.

An optimized sensor array 34 employs two or more types of such devices, or suitable substitutes, in appropriate combinations to achieve the desired profile of overall response. As depicted in FIG. 1, and further set forth in FIGS. 2-3, the sensors of sensor array 34 are arranged at different angles within vacuum chamber 310 and positioned to sense x-rays at different takeoff angles relative to the specimen 302 surface. While in the described version the sensors of array 34 are each embodied in a separate detector, this is not limiting and a large, multi-angle detector assembly may be used with two, three, four, or more sensors integrated into the detector assembly to create array 34. References to takeoff angles generally refer to the takeoff angle form the point where the beam 332 impinges on the sample 302, to the center of the relevant sensor. It is understood a sensor will actually detect x-rays over a range of takeoff angles which depends on its size in the vertical direction and its orientation. At least one of the mechanical support systems supporting and positioning the first and second detectors is adjustable to change the position and takeoff angle of the relevant sensor.

Figure 2:
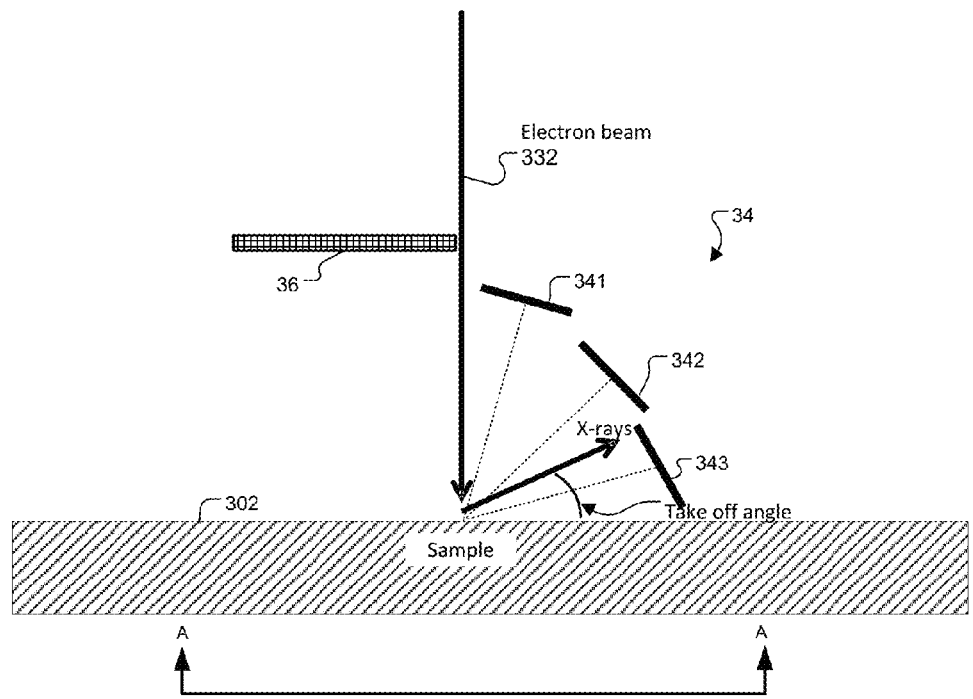
FIG. 2 is a diagram showing takeoff angle positions of various sensors from a side view according to another example embodiment.
Figure 3:
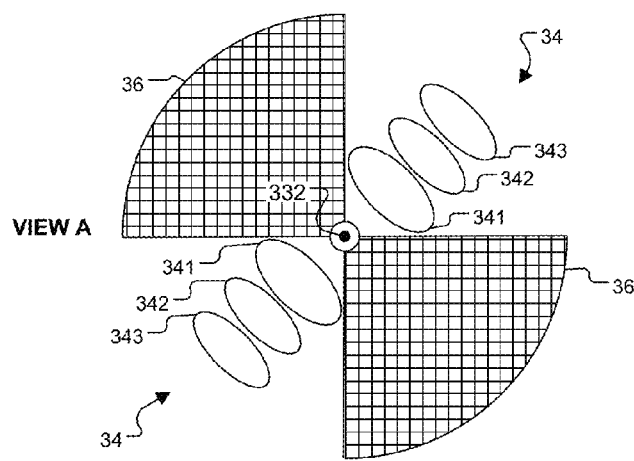
FIG. 3 shows a bottom view diagram taken along the view A-A of FIG. 2.

FIG. 2 is a diagram showing takeoff angle positions of various sensors from a side view according to another example embodiment, and FIG. 3 shows a bottom view diagram taken along the view A-A of FIG. 2.

Referring to FIGS. 1-3, sensor 341 is a first x-ray detector positioned within the vacuum chamber 310, including a first x-ray sensitive solid-state sensor sensitive to low energy x-rays and a first mechanical support system 350 supporting and positioning said first detector, including said first sensor, within said vacuum chamber positioned to sense x-rays at a high takeoff angle of between 90 degrees and 45 degrees relative the specimen surface, typically around 56 degrees, but preferably as high an angle as the sensor dimensions and surrounding structures allow. Sensor 342 in this version is a provided in a second x-ray detector positioned within the vacuum chamber, said second x-ray detector including a second x-ray sensitive solid-state sensor sensitive to high energy x-rays and a second mechanical support system 350, which may be integral to the first mechanical support system or may be a separate structure, supporting and positioning said second detector, including said second sensor, within said vacuum chamber. The second detector is positioned to sense x-rays at a low takeoff angle of between about 56 and 27 degrees relative the specimen surface.

FIG. 3 shows a bottom view of the diagram of FIG. 2, in which fewer backscattered electron detectors (BSE detectors) 36 are used to make room the x-ray sensors in array 34. In some versions such as the depicted version, the low energy x-ray sensor 341 may be positioned at a higher angle by removing or relocating the backscattered electron detectors 36, which in the version of FIG. 1 are shown positioned adjacent the column opening of the SEM 340. In FIG. 3, the BSE detectors 36 are shown with only two sections arranged adjacent to the electron beam filling two quadrants of the area around the column opening, leaving space in the other two quadrants for placing the EDS x-ray detectors. One possible configuration has two EDS x-ray sensors in each quadrant not occupied by the BSE detectors, with the EDS x-ray sensors laid out on a partial cone around the impinging electron beam, arranged at different take-off angles as described herein. For example, a configuration is provided in which the first sensor 341 has a take-off angle of 63.7 degrees and the second sensor 342 has a take-off angle of 26.3 degrees. The sensors are duplicated at an opposing side of the electron beam, however this is not limiting and other combinations of sensors may be employed at the opposite side.

Some versions may also include a third type x-ray sensor 343 positioned at a lower takeoff angle, lower than the first sensors 341 but and lower than the second sensor 342, within the vacuum chamber. The sensor 343 in this version is provided as a third x-ray detector including a third x-ray sensitive solid-state sensor having a thick beryllium window with a thickness of about 900 micrometers, but which may be 450-1000 micrometers, for example. In a three-sensor arrangement, the angular positions of first two sensor types, 341 and 342, may be adjusted to make room for the third sensor type. The third type sensor 343 as shown is at a lower takeoff angle than the other two sensors. Any suitable very-high energy detector may be employed, especially detectors built with SDD sensors sandwiched together. The third x-ray sensor 343 is provided as one or more separate detectors 343, each sensitive to very high energy x-rays and has a third mechanical support system 350 (which may be integral with the other support systems or separate) for supporting and positioning third detector, including said third sensor, within the vacuum chamber. The third sensors 343 are positioned to sense x-rays at a low takeoff angle of between about 56 and 27 degrees relative the specimen surface. As can be seen in the drawing, the higher energy sensors 342 and 343 may be positioned relatively closer to the beam 332 incident point on the sample, from which x-rays are emitted. In versions with a third sensor 343, it is positioned below the second sensor, which will typically require that the range of takeoff-angles available to position the individual second or third sensors is smaller. For example, the second sensors 342 may be positioned between about 41.5 degrees to about 56 degrees (with reference to the center of sensor), while the third sensors 343 may be positioned between about 27 degrees and about 41.5 degrees. These ranges are merely exemplary and other embodiments may use other ranges. For example, the version of FIG. 4, which mounts some of the array 34 x-ray sensors within the structure of the SEM focusing column, includes a higher takeoff angle of about 77 degrees for the first sensors 341, a takeoff angle of about 60 degrees for second sensors 342, and an angle of about 42 degrees for the third sensors 343, all with respect to the center of the sensors because the sensors span a range of angles.

Referring again to FIG. 1, while the sensors 341-343 are shown above one another at the same position along the vacuum chamber 310 walls, this is not limiting and preferred versions position the sensors at different locations in chamber 310. Preferably the third sensors are positioned at the lower takeoff angle that the second sensors, but in some versions they may be positioned at the same angle at different positions. In such cases, both the second and third sensors are positioned at a lower angle than the first sensors 341. As shown, sensor array 34 may include more than one of each type of sensor. For example, it is advantageous to provide more than one low-energy sensor 341 positioned at different locations around the column axis on which electron beam 332 is projected, all arranged within the range of takeoff angles described above. The two sensors 341 shown in FIG. 1 are an example of such an arrangement, which allows the system to better detect low energy x-rays compared with versions that have only one low energy sensor 341. Versions with three, four, five, six, or more of each sensor may be employed.

FIG. 4 shows a cross-sectional view 900, of a detector arrangement according to another embodiment of the present invention. X-ray trajectory vectors 951, 952 and 953 are shown as arrows going from the sample 902 to X-ray detectors 941, 942, and 943 respectively. Backscattered electron (BSE) trajectory vector 961 goes from the sample 902 to the BSE detector 936. The X-ray detectors 941, 942, and 943, and also the BSE detector 936, may all be annular to maximize collection efficiency, thus the trajectory vectors could be directed to any azimuthal positions azimuthally. X-ray detectors 941 and 942 are positioned adjacent to the electron beam column of an SEM, like that of FIG. 1, for example. In this embodiment, backscattered electrons 961 are prevented from reaching X-ray detectors 941, 942 and 943 by the electrostatic fields of the SEM column focusing lens, comprising electrodes 970, 972, and 973, which has a modified design as shown. Electrodes 970 and 972 are configured as cones, with their apexes near the sample position—this ensures that the solid angles subtended by electrodes 970 and 972 as "viewed" from the sample are minimized, thereby maximizing the collection efficiency of detectors 941 and 942 (which is proportional to their solid angles as "viewed" by the sample). The low-energy sensitive x-ray detectors 941 are placed very near the beam location (optical axis) of the column, and in this case are positioned above the lowermost portion of the focusing elements 970 and 972 of the column, inside of the focusing electrodes 972, and further above the lower ends of lens elements 970, which are preferably held at 0V in this embodiment. Focusing electrode 972, which may replace or supplement focusing elements of the SEM of FIG. 1 (condensing lens 356 and objective lens 358), are held at a large negative voltage sufficient to deflect BSEs 961 away from X-ray detectors 941 and 942. As shown, BSE detectors 936 are positioned with shields 973 between BSE detectors 936 and the sample 902, wherein shields 973 also form part of the focusing lens. The large negative voltage on focusing electrodes 972 deflects BSEs 961 on curved paths as shown around shields 973, allowing them to be detected on detectors 936, while the detectors 936 are shielded from x-rays (which travel in straight lines and strike shield 973). The very-high-energy X-ray detector 943 in this version is positioned at a low takeoff angle. Detector 943, in this version, is integrated with a BSE repeller electrode, which includes at least some of the supporting structure of detector 943 at a large negative voltage, similar to the voltage on focusing electrodes 972 (for example, about −16.1 kV, or a large negative voltage such as −16 kV or greater, or −20 kV or greater). A similar bias voltage may also be applied to detector 943. The voltage required on elements 972 and 943 will vary with the energy of the beam and the bias voltage of the sample, which in this case is held at 0V. The voltage should be set at a sufficiently large value to repel the backscattered electrons 961 away from the surface of detectors 943, and further curve them toward BSE detectors 936. Peltier coolers may be employed on the outer wall of the chamber or other suitable location(s) to extract heat from detectors 941, 942, and 943 through their supporting structures.

Detector 941 is positioned around electron beam 932 at a takeoff angle of about 79 degrees (where 90 degrees corresponds to X-rays leaving normally to the surface). Detector 942 is positioned with a takeoff angle of about 59 degrees. Detector 943 is at an angle of about 42 degrees. All three detectors 941, 942, and 943 span ranges of angles around these approximate center angles—the particular center angles are not part of the present invention. One embodiment according to this scheme may provide: 1) first detector 941 collecting X-rays emitted from the sample 902 within plus or minus 3 degrees of the listed takeoff angle, and 2) second detector 942 collecting X-rays emitted from the sample 902 within plus or minus 9 degrees of the listed takeoff angle. Third detector 943 may be employed with this embodiment with a center positioned within a takeoff angle range of about 37 degrees to 47 degrees. First 941, second 942, and third 943 detectors may each comprise a single detector element, or may be divided into one multiple segments, arrayed radially or azimuthally, or in a combination of both radial and azimuthal segments. Segmented detectors may enable higher X-ray count rates in cases where the multiple detector segments operate in parallel. It should be understood that while these specific detector takeoff angle positions for detectors 941, 942, and 943 are described, they may have other combinations of positions as described for the first, second, and third x-ray sensors 341, 342, and 343. For example, first detector 941 may be positioned within said vacuum chamber positioned to sense x-rays at a high takeoff angle of between about 45 degrees and 90 degrees relative the specimen surface. Second x-ray detector 942 may be positioned within said vacuum chamber to sense x-rays at a low takeoff angle of between about 27 and 56 degrees relative the specimen surface, and lower than the first detector takeoff angle. And a third x-ray detector 943 may be positioned to sense x-rays at a lower takeoff angle than the second detector 942.

As can be seen in FIG. 4, the second detectors 942 may be positioned with the detector surface not pointing directly toward the beam impact area on the sample 902, from which x-rays are emitted. This may allow a larger detector surface to be employed. Detector 942 as shown has a surface area in at least one dimension more than three times that of detectors 941. Other versions may use smaller detectors 942, and may align detectors 942 pointing at the x-ray emission area of the sample 902 over which electron beam 932 is scanned.

Figure 5:
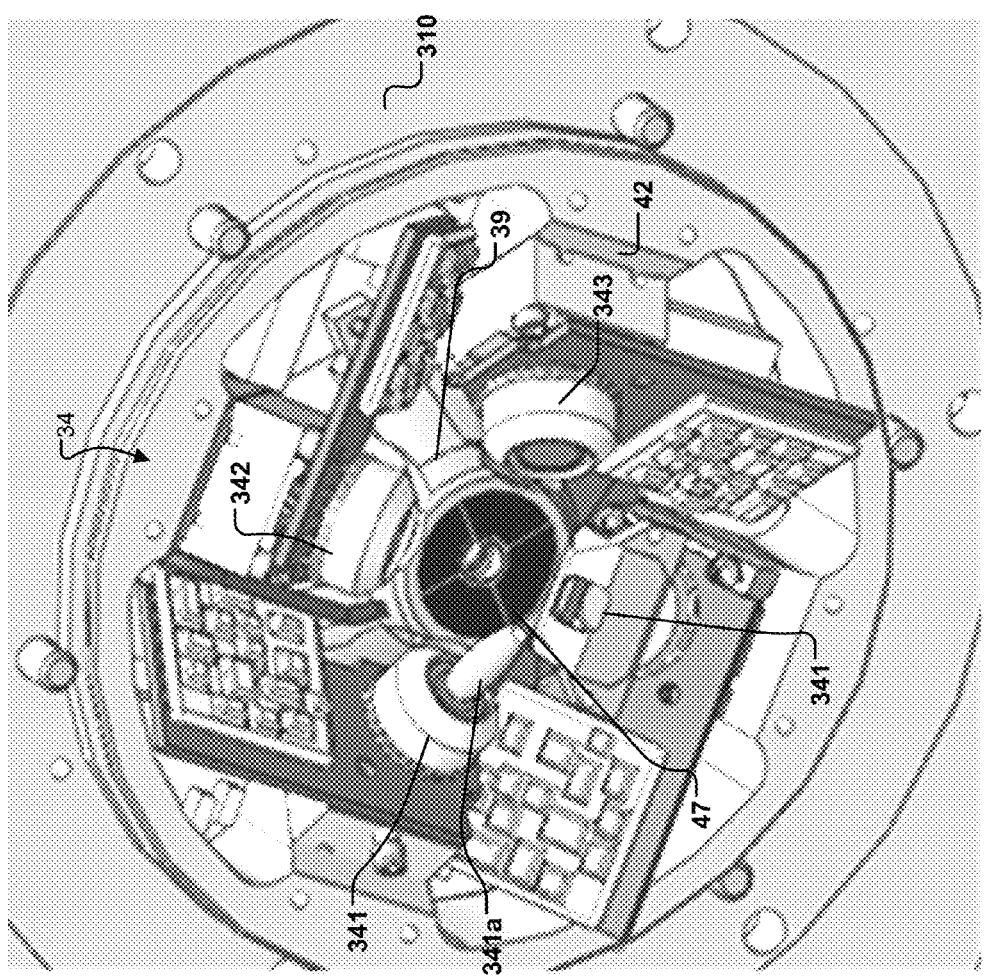
FIG. 5 is a perspective view of the underside of an SEM microscope focusing column with an array of four differentiated detectors mounted around the lower opening of the column along the top/sides of the vacuum chamber.

Referring to FIG. 5, the drawing shows a perspective view of the underside of an SEM microscope 340 focusing column with an array of four differentiated detectors mounted around the lower opening of the column along the top/sides of the vacuum chamber 310. Depicted is a column-integrated array of sensors 34 that incorporates four subassemblies 341, 341, 342, and 343. In this version, the sensors are embodied in separate detectors including associated detector electronics as described in U.S. Pat. No. 8,334,511, for example. These sensors include the lower depicted sensor 341, which is a conventional 5 mm2 UTW sensor with an electron trap, positioned at a first high takeoff angle which may be in any of the higher ranges discussed above. Another lower energy sensitive sensor 341 is provided in the left-hand depicted detector, this sensor being a special detector with 5 mm2 UTW and low-energy optical assembly 341a (the elongated tubular structure) affixed in front of the sensor for filtering out high energy x-rays. This second low-energy x-ray sensor 341 is also mounted at a high takeoff angle within the ranges described above. The top depicted detector in the FIG. 5 contains a sensor 342 which is a conventional 30 mm2 sensor with a Beryllium window, sensitive to mid-energy and high-energy x-rays as known in the art. This sensor 342 is preferably mounted at the middle (or low) range of takeoff angles as described above. The right-hand depicted detector houses sensor 343, which is a special (customized) 30 mm2 high-energy BeW sensor. In the center is a quadrant BSED 47.

As discussed, the detector subassemblies housing the depicted sensors may be constructed according to the teachings of U.S. Pat. No. 8,334,511, or other suitable detector subassembly designs, which are removably attached to a detector mounting interface flanges 42, which provides the appropriately-angled thermal mounting face. It will be understood after appreciating this specification that such modular subassemblies are of great benefit for arranging the detector array at the various takeoff angles, since all elements of the array can be installed and their alignment observed and adjusted separately from the remainder of the microscope.

In various embodiments, implementations of the angled detector array 34 involve special techniques to combine the results of the individual detectors into a complete analytical result. This involves merging the peak intensities extracted from each spectrum, adjusted for their takeoff angles, distances to the sample, integration times, and surface areas, and other characteristics of the detectors. The integration time constant for each individual sensor in array 34 may also be adjusted. Typical integration constants for the EDS signal range from 8 micro-seconds to nano-seconds, with the lower energy x-ray sensors using longer integration times such as 1-8 micro-seconds while the higher energy x-ray sensors use shorter integration times such as those in the 100 nano-second order of magnitude, typically less than 1 micro-second. The system in FIG. 1 may also be programmed to adjust the sensors in various measurement processes according to some embodiments of the invention.

Referring again to FIG. 1, output from the sensors 341-343 is amplified and sorted by the processor 320, which counts and sorts the total number of x-rays detected during a specified period of time, at a selected energy and energy resolution, and a channel width (energy range) of typically between 2.5 and 20 eV per channel. Processor 320 may include a computer processor; operator interface means (such as a keyboard or computer mouse); program memory 322 for storing data and executable instructions; measured spectra memory 323 for storing the measured data and final processed data; data template memory 324 for storing data to which the measured spectra may be compared to identify materials or to select further identification steps; spectra interface means for data input and output, executable software instructions embodied in executable computer program code; and display 35 for displaying the results of a multivariate spectral analysis by way of video circuit 342. Processor 320 may be a dedicated computer processor in specialized hardware having control interfaces for system 300, or may be a part of a standard laboratory personal computer, and is typically coupled to at least some form of computer-readable media. Computer-readable media, which include both volatile and nonvolatile media, removable and non-removable media, may be any available medium that can be accessed by processor 320. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 320. Program memory 322 can include computer storage media in the form of removable and/or non-removable, volatile and/or nonvolatile memory and can provide storage of computer-readable instructions, data structures, program modules and other data. Generally, the processor 320 is programmed by means of instructions stored at different times in the various computer-readable storage media of the computer. The invention described herein includes these and other various types of computer-readable storage media when such media contain instructions or programs for implementing the steps described below in conjunction with a microprocessor or other data processor. The invention may also include the computer processor itself when programmed according to the methods and techniques described herein.

While the embodiment shown includes a scanning electron microscope, related embodiment could use a transmission electron microscope or a scanning transmission electron microscope to generate x-rays from the sample. An x-ray fluorescence system could also be used to generate x-rays from the sample.

Figure 6:
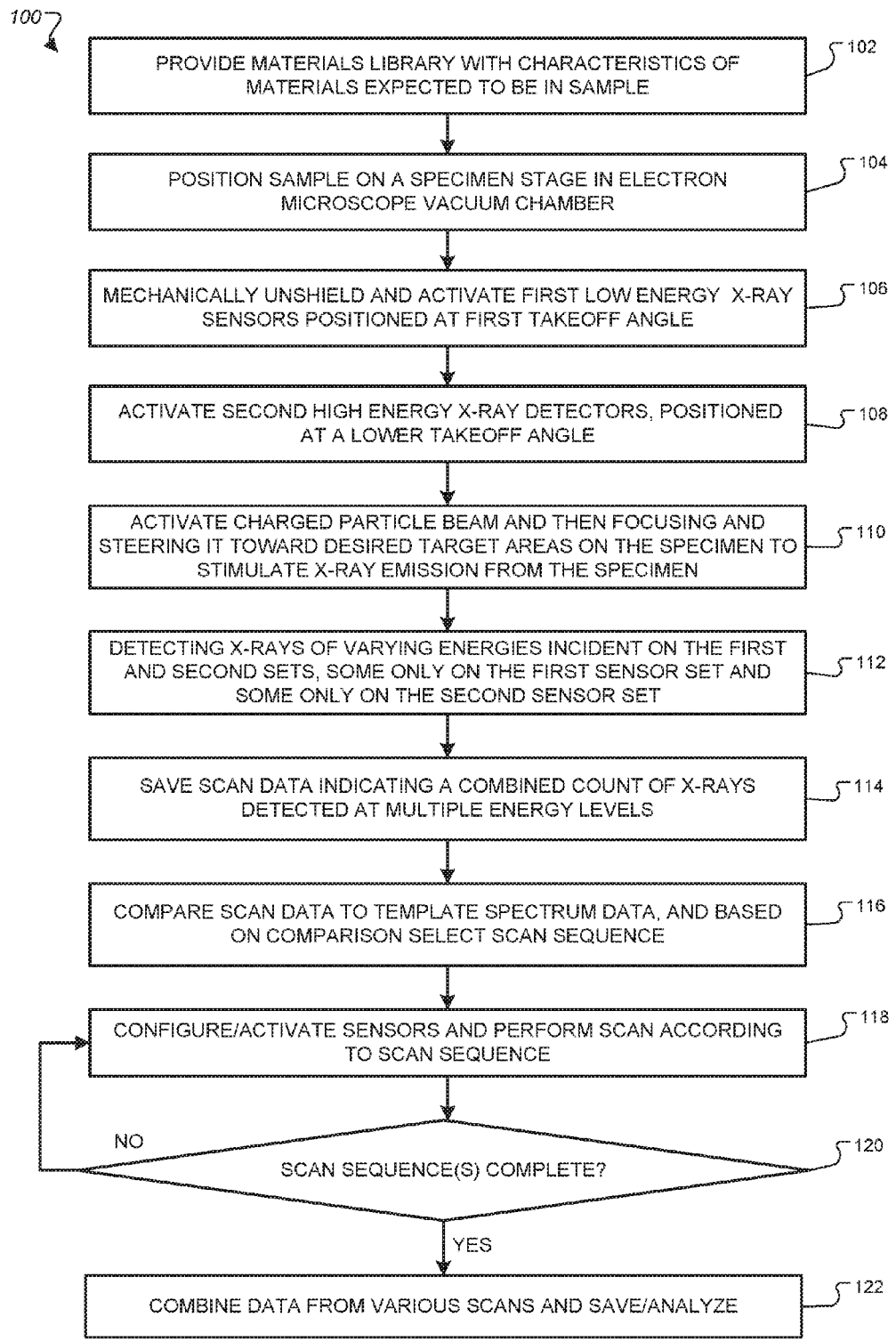
FIG. 6 is a flowchart of a process according to an example embodiment for operating an electron microscope to examine a specimen.

FIG. 6 is a flowchart of a process 100 according to an example embodiment for operating an electron microscope to examine a specimen. The microscope includes a vacuum chamber for holding the specimen. The process works with a materials library provided at block 102 that has the x-ray emission characteristics of materials expected to be in the sample. This may include metals, alloys, minerals, aggregates, organic tissue, individual elements, or other materials. The process next at block 104 includes positioning the sample on a specimen stage within the vacuum chamber. The process then at block 106 mechanically unshields and activates a first low energy x-ray sensor positioned at a first takeoff angle with respect to the sample. The unshielding portion of this block may include removing a cover that directly exposes the sensor surface, or removing a cover to expose an ultra-thin window over the sensor surface, as further described with respect to FIG. 7. Other versions of the process may use sensors that do not require the mechanically movable shielding on a low energy x-ray detector, but instead employ ultra-thin window detectors for the low-energy x-ray measurements, but follow a similar process of scanning as described below. The process also activates at least a second x-ray detector, positioned at a lower takeoff angle than the first x-ray detector, at block 108. The second x-ray detector is sensitive to higher energy x-rays than the first detector, and will usually have a broad sensitivity across the energy spectrum such as a conventional beryllium window detector (type two as described above). It may also be a high energy x-ray detector such as the type four high-energy SDD described above.

Then the process at block 110 activates the charged particle beam, and focuses and steers it toward desired target areas on the specimen to stimulate x-ray emission from the specimen. Typically the beam is scanned in a regular grid or raster pattern, or some variation thereof, to allow an image to be produced with the resulting data. While scanning the beam, the process at block 112 detects a first group of x-rays of varying energies incident on the first and second sensor sets, some of the x-rays detectable only on the first sensor set and some detectable on the second sensor set, and in response saves first scan data to memory at block 114, the first scanned data indicating a combined count of x-rays detected at multiple energy levels. Blocks 110 and 112 preferably operate with a pre-scan level timing that is faster than detailed scanning, for example operating the x-ray sensors over a shorter period than detailed, high energy-resolution scanning permits, or operating the x-ray sensors with shorter integration time constant settings than time constants used with detailed, high energy-resolution scanning. Blocks 110 and 112 may also scan the electron beam in a lower resolution (resolution of the image) pattern for this pre-scan step, as compared to the resolution employed for later, more detailed scans. Block 110 and 112 may also scan a small portion of the sample area, as compared to a more detailed scan which scans a larger portion. Variations of these features may be used in any subcombination to produce a desired "prescan mode."

After saving the first scan data at block 114, the process may compare the first scan data (block 116) to template spectrum data stored in a material library to determine a desired scan sequence for further, more detailed, x-ray scanning. This block may include comparing the first scan data to templates of x-ray scan data that include model spectrums of x-ray energy levels. Various templates are kept in a library, each based on a target material or materials that are expected to be encountered or examined. Separate templates may be provided for the same material scanned with different sensor arrangements, that is, the different numbers of sensors and take-off angles of sensors discussed herein. The templates are preferably formatted to allow for comparison to a pre-scan in which the x-ray sensors may be operated in one of the pre-scan modes discussed above with respect to blocks 110 and 112. The comparison at block 116 may use only selected x-ray energy levels, rather than all energy levels detected in first saved data, in order to identify the presence of key material on which decisions are based as to what scan procedure or scan sequence is desirable to scan the specimen in detail. The comparison may involve comparing a current configuration of the machine to recorded configurations in the x-ray template data to select only data taken under similar sensor configurations for comparison. The comparison may note closest matching values for selected energy levels, differences between the first scanned data and the template for selected energy levels, and other suitable comparison data. Based on the comparison, and possibly other system settings and user configuration settings, a scan sequence is selected. The scan sequence may be augmented to adjusted based on the comparison results, system configuration, or user input.

Next at block 118, the process, based on the selected scan sequence, performs the sequence by activating selected sensors from the first and second sensor sets, and activating the charged particle beam again and detecting a second group of x-rays incident on the selected sensors, some of the x-rays detectable on less than all of the selected sensors, and saving second scanned data. The scan sequence may involve more than one scan with different groups of sensors activated, different sensor configurations, sensors moved to different takeoff angles, and other variations, as indicated at block 120 where the process checks if the scan sequence is complete and if not returns to block 118 for further scans. The scans at this block are typically detailed, high resolution (dimensional) scans but the sequence may include other types of scans such as a low resolution scan to locate a feature of a particular material and a high resolution scan of that feature. The scans of the scan sequence may be high energy-resolution scans, which may be relatively slow especially for collection of low energy x-rays with the low energy x-ray sensor(s). For example, the first set of low energy sensors are operated with a relatively long integration time of 1 to 8 micro-seconds, while the first set of high energy sensors is operated with a relatively short integration time constant of less than one micro-second. The scan sequence may involve mechanically activating a low energy sensor by moving its shield mechanically, similarly to block 106, and shielding it again after the scan by moving the shield back over the sensor mechanically.

When the scan sequence is complete at block 120, the process goes to block 122 where it combines the data from the various scans and saves or displays it for analysis. This may include scaling count data received based on relative numbers of sensors at each takeoff level. This block may also include scaling or adjusting the data relative to the takeoff angle of the sensor to account for the increased presence of x-rays at high takeoff angle positions. This may also include identifying amounts of some elements present in the sample based on data only obtained from the first x-ray sensors, and identifying other amounts of elements present in the sample based on data only sensed by the second sensors.

The method may also include activating a third set of one or more solid-state sensors sensitive to low energy x-rays at blocks 106 and 108, the third set positioned within the vacuum chamber at an lower takeoff angle than that of the second set of sensors. The method then measures x-rays with the third set of x-ray sensors. The method may also include adjusting the takeoff angle of at least one of the one or more sensors in the first, second, or third sets of sensors. This may be done before the first scan or between any two scans in the method. The angle may be adjusted to raise the angle or lower the takeoff angle. Some sensor angles may be raised while others are lowered.

Figure 7:
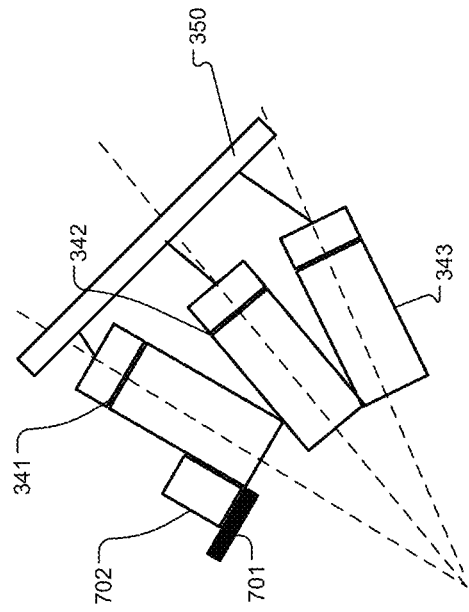
FIG. 7 is a block diagram depiction of a sensor array in which one of the low energy sensors includes an adjustable shield.
Figure 7:
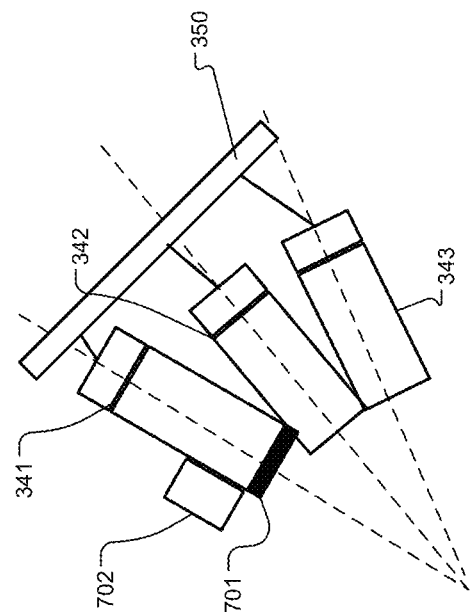

FIG. 7 is a block diagram depiction of a sensor array 34 in which one of the low energy sensors includes an adjustable shield. In some embodiments, at least one of the first set of low energy solid-state sensors 341 includes a shield or cover 701 mechanically adjustable under control of the system processor 320 to move to a first position as depicted on the left shielding the sensor, and second position as depicted on the right allowing x-rays to reach the sensor. The movement may be accomplished, for example, by an actuator 702 coupled to the shield 701. In use, it can be understood that the sensors 341 comprise at least one windowless sensor that is controlled to enter a first low energy sensing mode by opening a cover exposing the sensor to the x-rays, and controlled to enter a second mode by closing a cover blocking x-rays from the sensor.

Figure 8:
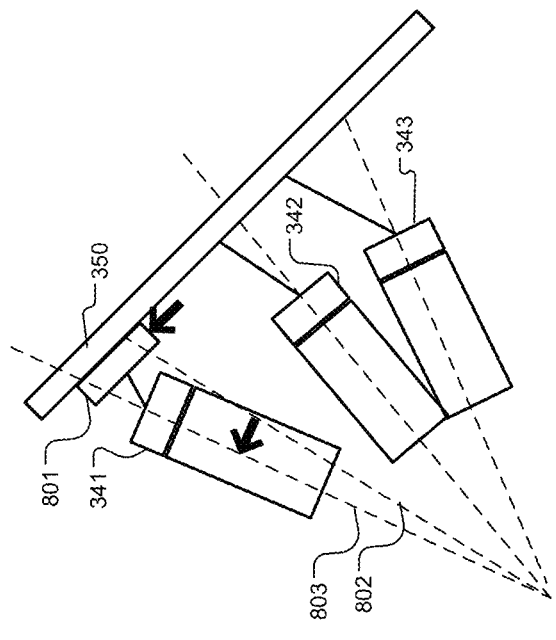
FIG. 8 is a similar block diagram of sensor array in which the mechanical support system is adjustable to change the effective takeoff angle of a sensor.
Figure 8:
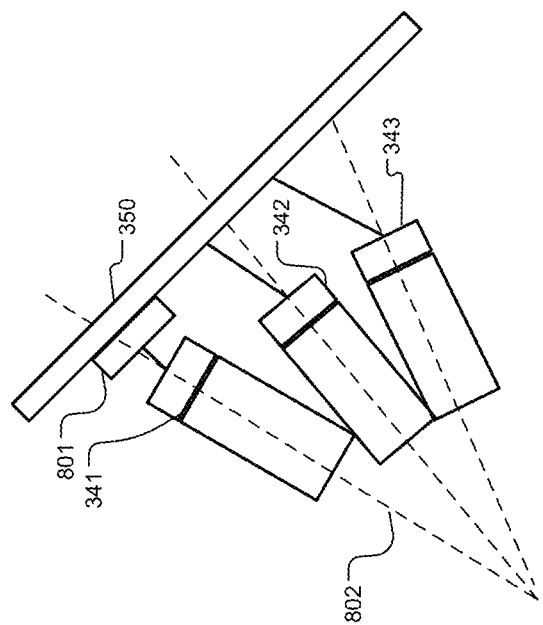

FIG. 8 is a similar block diagram of sensor array 34 in which the mechanical support system is adjustable to change the effective takeoff angle of a sensor. In this embodiment the low power x-ray sensor 341 is shown as adjustable, however in various embodiments any or all of the sensors may be made adjustable with the mechanical support system 350. A track or other sliding arrangement may be used to movably connect the sensor to the mount, and still allow the desired thermal transfer required to operate these sensors. Thermal coupling grease may also be employed, as it is in some fixed embodiments, to thermally couple the movable portion of mechanical support system 350 to the fixed portion. As shown, mechanical support system 350 includes a linear movement actuator 801, which may move along a curved track such that the sensor is always facing the emission point of x-rays. A separate pivoting angle adjustment may instead be used with a straight track, with the movement made by moving the mounting position of sensor 341 higher up the inside wall of the chamber as shown by the arrows in the left-hand drawing, and the angle of sensor 341 adjusted to point its takeoff angle axis, originally at 802, to the new higher angle as depicted by the dotted line 803 directly toward the x-ray emission point or area where the electron beam hits the target in the beam's center position. While these two methods of adjusting the sensor takeoff angle are discussed, other versions may use other suitable structures to adjust the takeoff angle. Actuators may be employed to effect the movement described under vacuum, without requiring an operator to open the vacuum chamber and manually adjust the sensor positions.

Figure 9:
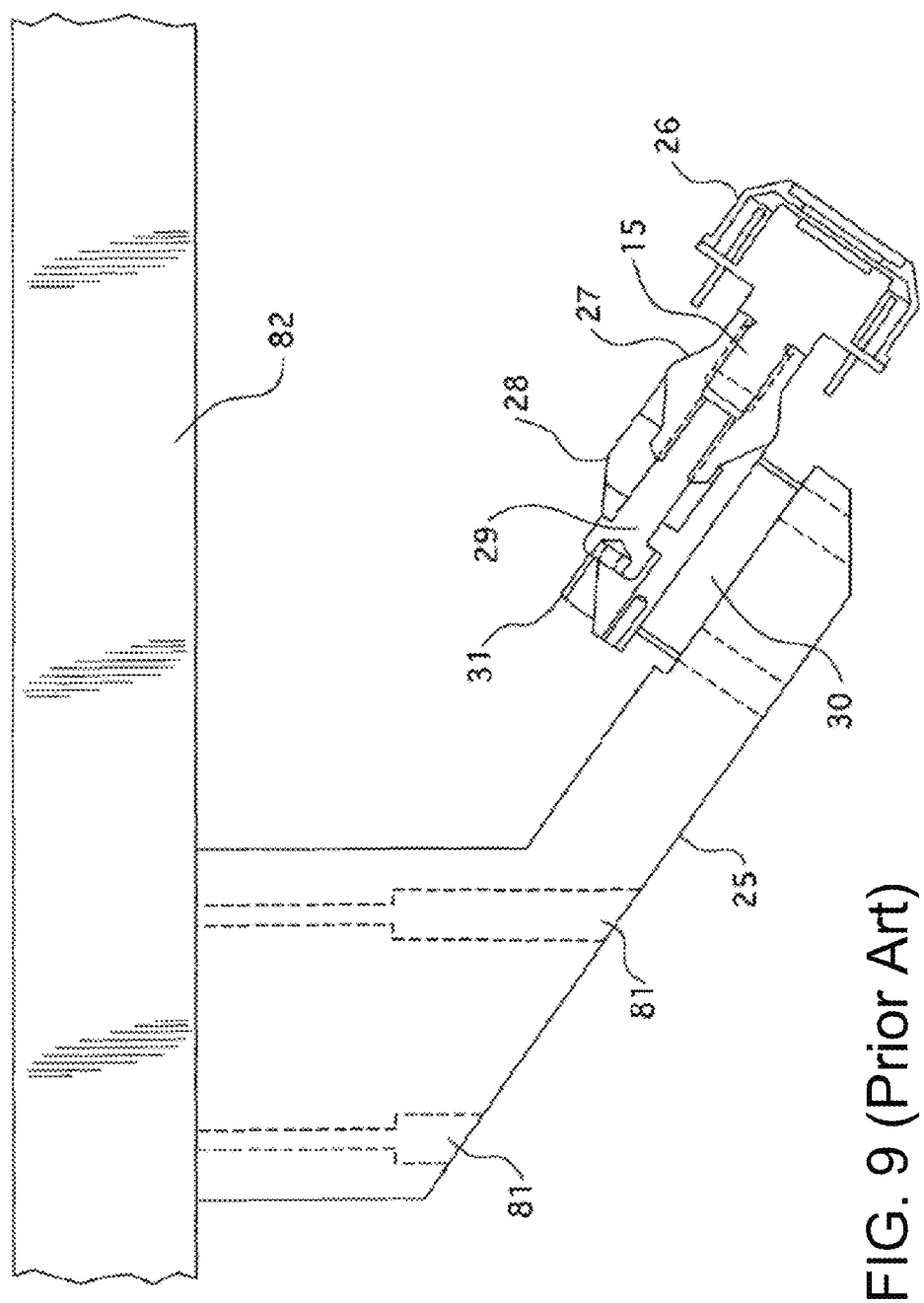
FIG. 9 is a cross sectional diagram of a prior art mechanical support system holding a sensor of a very basic implementation of an integrated EDX detector constructed with a packaged SDD sensor module, which detector may be employed to advantage with the techniques herein.

FIG. 9 is a cross sectional diagram of a prior art mechanical support system holding a sensor of a very basic implementation of an integrated EDX detector constructed with a packaged SDD sensor module. This design and related features are further described in U.S. Pat. No. 8,334,511, mentioned above, and may be employed to advantage in combination with many of the features described herein. The depicted mounting bracket 25 is one version of a mechanical support structure as discussed herein, and is designed to be attached to the flat "ceiling" surface of the specimen chamber 82 of a particular SEM by means of screw passage holes 81 provided. The detector element is a packaged SDD module 26. The dimensions of the mounting bracket 25 are chosen such that the SDD module 26 is held in the desired proximity to the specimen with its axis pointing at the nominal impingement point of the microscope's electron beam on the specimen. The threaded thermal stud 15 of the packaged SDD module 26 is screwed tightly into a tapped hole located in the front of the thermal interface stub 27 whose rear portion is tapered and provided with a central tapped hole. The role of the thermal interface stub is to provide an efficient thermal bridge between the packaged SDD module 26 and the cold plate 28. The cold plate incorporates a mating tapered bore in its front face into which the tapered rear of the thermal stud is inserted. A screw 29 inserted through the rear of the cold plate (28 pulls the thermal interface stub 27 into intimate contact with the cold plate, a good thermal contact being abetted by the conical tapers of the two parts. The cold plate 28 in turn clamps a TEC module 30 tightly to the front lip of the mounting bracket 25 by means of the four clamping screws 31.

The function of this arrangement is to efficiently extract heat from the detector module 26 and, by means of the TEC element 30, to transfer it to the mounting bracket 25, which in turn conducts it to the structure of the specimen chamber 82, where it is distributed through the substantial thermal mass of the specimen chamber and dissipated by convection from its surface and by conduction to associated structures. In versions in which the sensor angle and position are adjustable using an actuator, a mounting slide made of metal or other suitable heat conductive material may be positioned between bracket 25 and the chamber wall 82. Since the amount of heat that is extracted from the packaged SDD module 26 is rather small, the additional heat generated by the thermoelectric circuit does not appreciably raise the temperature of the specimen chamber, and this can be minimized, if required, by making external provisions to facilitate convection and/or conduction of such excess heat from the microscope. Such provision may be as simple as providing structural elements, such as fins attached to the specimen chamber, that facilitate convective cooling. In the specific microscope for which this implementation was designed, an external forced-air source ensures a flow of ambient air over the specimen chamber, and this provision alone has thus far been found to be an adequate means of dissipating the minimal heat generated. In an extreme case, such as might be presented by an instrument intended for operation in an especially hot environment, a fluid-based heat exchanger or refrigeration device could be employed to cool the specimen chamber. The salient point is that such provisions for cooling of the specimen chamber of a microscope designed with this requirement in mind can be accomplished much more readily than the problem of dealing with the "spot cooling" of a conventional x-ray detector mounted on a conventional electron microscope.

Note that the specimen chamber of an electron microscope must necessarily be maintained under a relatively high vacuum while in operation and thus there is essentially no convective transfer of heat between any of its internal components. On the one hand, this is advantageous because it minimizes the parasitic transfer of heat to the cooled sensor device. However, the lack of air molecules to transfer heat across small gaps makes it essential that there is intimate mechanical contact between the various elements of the thermal circuit. Ensuring such contact is the purpose of the tapered interface between the thermal interface stub 27 and the cold plate 28. It is also essential that the cold plate 28 and the mounting bracket 25 make good thermal contact with the opposing faces of the TEC module 30. Techniques for providing a good thermal interface between surfaces are well known in the art. Careful preparation of the surfaces to ensure that they are free from surface irregularities is essential, but not sufficient. There exist a variety of thermal "grease" compounds as well as compressible thermal contact pads or deformable foils which are designed to be used between thermal elements to bridge any remaining gap irregularities. Of course, any such material must be selected carefully to ensure that it is compatible with vacuum usage.

The materials chosen for structures in the thermal path also play a role in the success of this scheme. In the preferred implementation illustrated, the thermal interface stub 27 and the cold plate 28 are fabricated from copper. The mounting bracket 25 is fabricated from aluminum. Both of these materials are notably good thermal conductors. On the other hand, the screws used to clamp the detector to the mounting bracket should not provide an efficient thermal path for transfer of heat across the TEC module. Stainless steel screws are an acceptable choice, due to the rather poor thermal conductivity of this material. Screws fabricated from a mechanically-strong low-outgassing plastic such as PEEK or Vespel are an even better choice, and PEEK screws are employed in the preferred implementation.

In order for the SDD device to operate per specifications, its sensor element must be maintained at a temperature of approximately −20° C. Thus, it is necessary to provide a temperature reduction of approximately 45° C. between the ambient temperature of a typical laboratory environment (−25° C.) and the SDD sensor element. The TEC device 30 internal to the SDD module 20 could, in principle, provide this differential. However, the practical reality is that one cannot rely on the detector having access to this low an ambient temperature in order to sink the heat it generates. For example, one particular EM instrument designed for non-laboratory operation is specified for ambient operating temperatures as high as 35° C., and after making allowance for higher temperatures within the case of the instrument, the internal ambient temperature may be in excess of 40° C. It is well known that the efficiency of a TEC device declines rapidly with increasing temperature differential. For example, a specific TEC module driven by 0.6 amps of current provides 2.43 watts of cooling across an 18° C. temperature differential, and only 0.25 watts of cooling across a 60° C. differential. Thus, it is impractical for a single-stage TEC module to provide the large temperature differential that is required for an SDD detector to be operated for best performance in a warm environment. The conventional approach is to employ an external TEC element, mounted exterior to the microscope, which removes heat from a long cold finger that receives the heat from the SDD module, and which the external TEC element then transfers its heat to convective fins incorporated in the case of the detector exterior to the microscope, whereby the heat is dissipated to the ambient air. However, this approach is not ideal in that: (1) the cold finger represents a substantial thermal mass that must be cooled to a suitable temperature on start up. Further, a certain amount of parasitic heat "leakage" to the cold finger by both radiation and conduction is inevitable by virtue of the fact that the cold finger is supported in close proximity to its tubular enclosure and that the cold finger must penetrate the specimen chamber of the microscope through some kind of vacuum seal. Such a parasitic heat transfer acts to increase the demands placed on the external TEC module, requiring it to dissipate a greater amount of heat. (2) A conventional detector design has few practical options for increasing the thermal dissipation from the hot side of its external TEC device. Electron microscopes have not generally been designed with any provision for thermal management of the detector environment and, due to the extreme vibration sensitivity of these instruments, the incorporation of fans within the EDX detector unit is strongly discouraged. Thus, the only practical option for ensuring adequate heat dissipation in warm environments is to incorporate extra-large fins on the external detector case to enhance passive convective cooling. Since the detector is often mounted in a very crowded area of the microscope, such large cooling fins are undesirable, and there is no certainty that they will receive adequate air flow in any case. By contrast, the simple design illustrated here minimizes these issues. There is a very minimal thermal mass interposed between the packaged SDD module 26 and the secondary TEC module 30, and there is little opportunity for parasitic heat transfer. Further, to the degree that the support bracket 25 is warmer than the specimen chamber, parasitic heat transfer actually aids the function of carrying heat away from the sensor. Consequently, there are some useful thermal efficiencies inherent to this type of design. It will also be readily apparent that it is a far simpler mechanical problem to provide a good thermal path to the specimen chamber than it is to provide an isolated path to an external sink while penetrating the specimen chamber wall. Lastly, it is to be noted that it is generally a simpler problem to dissipate an amount of heat from the rather substantial vacuum chamber of the electron microscope than it is to control the temperature in the specific locale of the detector. That is to say, by practicing thermal management as an issue associated with the microscope design, rather than just the concern of the detector manufacturer, more efficient and reliable thermal performance can be realized.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Although the present invention and its advantages have been described in detail, it should be understood that various changes, substitutions and alterations can be made herein without departing from the spirit and scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An electron microscope comprising:
a vacuum chamber for containing a specimen to be analyzed;
an optics column, including an electron source and a final probe forming lens, for focusing electrons emitted from said electron source;
a specimen stage positioned in said vacuum chamber under said probe forming lens for holding the specimen;
a first x-ray detector positioned within said vacuum chamber, said first x-ray detector including a first low energy x-ray sensitive solid-state sensor sensitive to low energy x-rays and a first mechanical support system supporting and positioning said first detector, including said first sensor, within said vacuum chamber positioned to sense x-rays at a high takeoff angle of between about 45 degrees and 90 degrees relative the specimen surface, said first low energy sensor comprises a windowless sensor that is controlled to enter a first low energy sensing mode by opening a cover exposing the sensor to the x-rays, and controlled to enter a second mode by closing a cover blocking x-rays from the sensor; and
a second x-ray detector positioned within said vacuum chamber, said second x-ray detector including a second high energy x-ray sensitive solid-state sensor sensitive to high energy x-rays and a second mechanical support system supporting and positioning said second detector, including said second sensor, within said vacuum chamber positioned to sense x-rays at a low takeoff angle of between about 27 and 56 degrees relative the specimen surface, and lower than the first detector takeoff angle.

2. The electron microscope of claim 1 further comprising a third x-ray detector positioned within said vacuum chamber, said third x-ray detector including a third x-ray sensitive solid-state sensor having a thick beryllium window with a thickness of between 450-1000 micrometers and sensitive to very high energy x-rays and a third mechanical support system for supporting and positioning said third detector, including said third sensor, within said vacuum chamber positioned to sense x-rays at a lower takeoff angle than the second detector.

3. The electron microscope of claim 1 in which said first low energy sensor comprises a collimator mounted above a sensor surface and configured for blocking x-rays at designated blocked energy levels, and passing x-rays at designated passing energy levels through to the sensor surface for detection.

4. The electron microscope of claim 1 in which said first low energy sensor is positioned inside of an arrangement of focusing electrodes of the optical column and further positioned above the lower ends of lens elements of the optics column.

5. The electron microscope of claim 1 in which the second high energy sensor comprises a silicon drift detector (SDD) sensor electrode having a large thickness of approximately 450-1000 micrometers.

6. The electron microscope of claim 1 in which at least one of the mechanical support systems supporting and positioning the first and second detectors is adjustable to change the position and takeoff angle of the relevant sensor.

7. The electron microscope of claim 1 further comprising a backscattered electron detector attached within said vacuum chamber to said support system.

8. An electron microscope comprising:
a vacuum chamber for containing a specimen to be analyzed;
an optics column, including an electron source and a final probe forming lens, for focusing electrons emitted from said electron source;
a specimen stage positioned in said vacuum chamber under said probe forming lens for holding the specimen;
a first x-ray detector positioned within said vacuum chamber, said first x-ray detector including a first low energy x-ray sensitive solid-state sensor sensitive to low energy x-rays and a first mechanical support system supporting and positioning said first detector, including said first sensor, within said vacuum chamber positioned to sense x-rays at a high takeoff angle of between about 45 degrees and 90 degrees relative the specimen surface, in which the first low energy sensor comprises an ultra-thin window sensor fitted with x-ray optic that passes only x-rays in the range of energies released from the elements Li, B, C, N, O, and F; and
a second x-ray detector positioned within said vacuum chamber, said second x-ray detector including a second high energy x-ray sensitive solid-state sensor sensitive to high energy x-rays and a second mechanical support system supporting and positioning said second detector, including said second sensor, within said vacuum chamber positioned to sense x-rays at a low takeoff angle of between about 27 and 56 degrees relative the specimen surface, and lower than the first detector takeoff angle.

9. A method of examining a specimen using an electron microscope having a vacuum chamber for holding the specimen, the method comprising:
(a) positioning the sample on a specimen stage within the vacuum chamber;
(b) activating a first set of one or more low energy x-ray sensors, including mechanically unshielding at least one of the low energy x-ray sensors;
(c) activating a second set of one or more high energy x-ray sensors, positioned to receive x-rays at a lower takeoff angle than that of a position of the first set of sensors;
(d) activating a charged particle beam and then focusing and steering it toward desired target areas on the specimen to stimulate x-ray emission from the specimen;
(e) while performing (d) detecting a first group of x-rays of varying energies incident on the first and second sensor sets, some of the x-rays detectable only on the first sensor set and some detectable on the second sensor set, and in response saving first scan data indicating a combined count of x-rays detected at multiple energy levels.

10. The method of claim 9, further comprising:
comparing the first scan data to a material library to determine a desired scan sequence for detailed x-ray scanning;
based on the scan sequence, activating selected sensors from the first and second sensor sets;
activating the charged particle beam again and detecting a second group of x-rays incident on the selected sensors, some of the x-rays detectable on less than all of the selected sensors.

11. The method of claim 10, in which the first set of low energy sensors are operated with a relatively long integration time of about 1 to 8 micro-seconds, while the first set of high energy sensors is operated with a relatively short integration time constant of less than one micro-second.

12. The method of claim 9, further comprising scaling or adjusting the data relative to the takeoff angle of the sensor to account for the increased presence of x-rays at high takeoff angle positions.

13. In combination, an electron microscope and multiple x-ray detectors, said microscope including a vacuum chamber containing a specimen stage for holding a specimen to be analyzed; and said x-ray detectors including a first set of one or more low energy solid-state sensors sensitive to low energy x-rays, positioned within said vacuum chamber to sense x-rays at a high takeoff angle of between 45 degrees and 90 degrees relative the specimen surface, and a second set of one or more high energy solid-state sensors sensitive to high energy x-rays, positioned within said vacuum chamber to sense x-rays at a low takeoff angle of between 27 and 56 degrees relative the specimen surface, and lower than the take off of the first set of sensors;
wherein at least one of said first set of low energy solid-state sensors includes a shield mechanically adjustable under control of a system processor to move to a first position shielding the sensor and second position allowing x-rays to reach the sensor.

14. The combination of claim 13, further comprising a third set of one or more solid-state sensors sensitive to high energy x-rays, positioned within said vacuum chamber at a low takeoff angle of between 27 and 56 relative to the specimen surface.

15. The combination of claim 13, including an adjustable mechanical support for said x-ray detectors, the adjustable mechanical support system operable under control of a system controller and allowing adjustment to the takeoff angle position of at least one of the sensors relative to the specimen surface while the vacuum chamber is closed.

16. The combination of claim 13, in which the first set of one or more low energy solid-state sensors comprises an ultra-thin window sensor fitted with x-ray optic that passes only x-rays at energies released from the elements Li, B, C, N, O, and F.

17. The combination of claim 13, further comprising a backscattered electron (BSE) detector positioned within the vacuum chamber near an electron beam entry location, where the BSE detector includes two sections in two quadrants of the area surrounding the beam entry location, and leaving gaps in the other two quadrants, and wherein the first set of low energy x-ray sensors are positioned close to the electron beam entry location at least partly in the gaps provided by the BSE in the other two quadrants.

18. The combination of claim 13, in which the first set of low energy solid-state sensors comprises one or more collimators mounted above a sensor surface of a respective one or more of the low energy solid state sensors and configured for blocking x-rays at designated blocked energy levels, and passing x-rays at designated passing energy levels through to the sensor surface for detection.

19. The combination of claim 13 in which the second set of high energy solid-state sensors comprises at least one sensor constructed with multiple layers of silicon-drift detector (SDD) sensor electrode, each layer activatable to detect x-rays that reach it.

* * * * *